(12) United States Patent
Karandikar

(10) Patent No.: US 10,189,798 B2
(45) Date of Patent: Jan. 29, 2019

(54) ANTIMICROBIAL COMPOUNDS, METHODS OF MAKING THE SAME AND ARTICLES COMPRISING THEM

(71) Applicant: MEDICAL TECHNOLOGY RESEARCH INC, Woodburn, OR (US)

(72) Inventor: Bhalchandra M. Karandikar, Woodburn, OR (US)

(73) Assignee: MEDICAL TECHNOLOGY RESEARCH INC, Woodburn, OR (US)

( * ) Notice: Subject to any disclaimer, the term of this patent is extended or adjusted under 35 U.S.C. 154(b) by 0 days.

(21) Appl. No.: 15/516,374

(22) PCT Filed: Sep. 30, 2015

(86) PCT No.: PCT/US2015/053354
§ 371 (c)(1),
(2) Date: Mar. 31, 2017

(87) PCT Pub. No.: WO2016/054284
PCT Pub. Date: Apr. 7, 2016

(65) Prior Publication Data
US 2018/0134672 A1 May 17, 2018

Related U.S. Application Data

(60) Provisional application No. 62/115,854, filed on Feb. 13, 2015, provisional application No. 62/071,798, filed on Oct. 3, 2014, provisional application No. 62/071,722, filed on Oct. 1, 2014.

(51) Int. Cl.
| | | |
|---|---|---|
| C07D 251/20 | (2006.01) | |
| A61K 31/53 | (2006.01) | |
| C07D 251/16 | (2006.01) | |
| C07D 251/32 | (2006.01) | |
| A01N 43/66 | (2006.01) | |
| A01N 59/16 | (2006.01) | |

(52) U.S. Cl.
CPC ........... *C07D 251/20* (2013.01); *A01N 43/66* (2013.01); *A01N 59/16* (2013.01); *A61K 31/53* (2013.01); *C07D 251/16* (2013.01); *C07D 251/32* (2013.01)

(58) Field of Classification Search
CPC .................................................. C07D 251/20
USPC .......................................................... 514/183
See application file for complete search history.

(56) References Cited

U.S. PATENT DOCUMENTS

| | | |
|---|---|---|
| 3,682,909 A | 8/1972 | Hagemann |
| 3,689,651 A | 9/1972 | Argabright et al. |
| 3,852,220 A | 12/1974 | Kimmel et al. |
| 3,979,382 A | 9/1976 | Martinez-Alvarez et al. |
| 7,807,661 B2 | 10/2010 | Ylitalo et al. |
| 2004/0146567 A1 | 7/2004 | Taniguchi et al. |
| 2005/0266081 A1 | 12/2005 | Rogozinski |
| 2007/0003603 A1 | 1/2007 | Karandikar et al. |
| 2015/0313912 A1 | 11/2015 | Karandikar |

FOREIGN PATENT DOCUMENTS

| | | | |
|---|---|---|---|
| DE | 2536679 A1 * | 3/1976 | ........... C07D 251/34 |
| DE | 2536679 A1 | 3/1976 | |
| GB | 1464195 A | 2/1977 | |
| WO | 2005123699 A1 | 12/2005 | |
| WO | 2006015317 A2 | 2/2006 | |
| WO | 2014179353 A1 | 11/2014 | |

OTHER PUBLICATIONS

Rukevich et al. Zhurnal Obshchei Khimii (1980), 50(6), 1393-7.*
Hickmott, P., "Reactive Dyes: Preparation of Substituted Styrylpyrimidines and Styryl-s-Triazines," Journal of Applied Chemistry, vol. 16, No. 8, Aug. 1966, 3 pages.
Fattakhov, S. et al., "Synthesis of Some 1-Alkyl 3,5-Bis(ω-haloalkyl) Isocyanurates," Russian Journal of General Chemistry, vol. 71, No. 7, Jul. 2001, 5 pages.
Seifer, G., "Cyanuric Acid and Cyanurates," Russian Journal of Coordination Chemistry, vol. 28, No. 5, May 2002, 24 pages.
Blotny, G., "Recent applications of 2,4,6-trichloro-1,3,5-triazine and its derivatives in organic synthesis," Tetrahedron, vol. 62, No. 41, Oct. 2006, available online Aug. 14, 2006, 16 pages.
Yudin, N. et al., "Synthesys of Nitro-Derivatives of Biurut and their Salts," Proceedings of the 2007 10th Seminar on New Trends in Research of Energetic Materials, Apr. 25, 2007, Pardubice, Czech Republic, 5 pages.
Mahapatra, S. et al., "Silver nanoparticle in hyperbranched polyamine: Synthesis, characterization and antibacterial activity," Materials Chemistry and Physics, vol. 112, No. 3, Dec. 20, 2008, available online Aug. 20, 2008, 6 pages.
Almalioti, F. et al., "Convenient syntheses of cyanuric chloride-derived NHC ligands, their Ag(I) and Au(I) complexes and antimicrobial activity," Dalton Transactions, vol. 42, No. 34, Jul. 2, 2013, 11 pages.
ISA Korean Intellectual Property Office, International Search Report and Written Opinion Issued in Application No. PCT/US2015/053354, dated Jul. 27, 2016, WIPO, 15 pages.
Close, W., "Anticonvulsant Drugs. VII. Some Monosubstituted Isocyanurates," Journal of the American Chemical Society, vol. 75, No. 15, Aug. 1, 1953, 2 pages.

(Continued)

*Primary Examiner* — Kahsay Habte
(74) *Attorney, Agent, or Firm* — McCoy Russell LLP

(57) ABSTRACT

The present disclosure pertains to antimicrobial compounds that include silver (Ag) and an s-triazine ring with substitutions at nitrogen or carbon atoms of the s-triazine ring. In one example, the antimicrobial silver s-triazine may be readily incorporated in a variety of compositions and devices in both medical and non-medical settings. In another example, the said compounds may possess broad spectrum antimicrobial activity against bacteria, viruses, fungi and other microbes.

12 Claims, 3 Drawing Sheets

(56) References Cited

OTHER PUBLICATIONS

Argabright, P. et al., "Chemistry of Isocyanurates. I. Synthesis of Disubstituted Isocyanuric Acids from the Reaction of Alkali Metal Cyanates with Organic Isocyanates," Journal of Organic Chemistry, vol. 35, No. 7, Jul. 1, 1970, 5 pages.

Abu-Salem, Q., "1,3-Dimethylcyanuric Acid Derivatives," Doctor of Natural Science Dissertation, Institut für Anorganische Chemie, Fakultät für Chemie und Pharmazie der Eberhard-Karls-Universität Tübingen, Germany, Apr. 6, 2009, 158 pages.

European Patent Office, Extended European Search Report Issued in Application No. 15845821.6, dated May 16, 2018, Germany, 9 pages.

\* cited by examiner

ANTIMICROBIAL COMPOUNDS, METHODS OF MAKING THE SAME AND ARTICLES COMPRISING THEM

CROSS-REFERENCE TO RELATED APPLICATIONS

The present application is a U.S. National Phase of PCT Application No. PCT/US2015/053354 entitled "ANTIMICROBIAL COMPOUNDS, METHODS OF MAKING THE SAME AND ARTICLES COMPRISING THEM", filed on Sep. 3, 2015. PCT Application No. PCT/US2015/053354 claims priority to U.S. Provisional Patent Application No. 62/071,722, filed on Oct. 1, 2014, U.S. Provisional Patent Application No. 62/071,798, filed on Oct. 3, 2014, and U.S. Provisional Patent Application No. 62/115,854, filed on Feb. 13, 2015. The entire contents of the above-referenced applications are hereby incorporated by reference for all purposes.

FIELD OF THE INVENTION

The present invention pertains to antimicrobial compounds that include silver (Ag) and at least one s-triazine ring. The said compounds have broad applications in imparting antimicrobial property to amorphous compositions and articles of manufacture both in medical and non-medical settings. The heterocyclic s-triazine ring in the said compounds permits adding chemical groups to the compounds to tailor their properties.

BACKGROUND OF THE INVENTION

Although silver metal in itself does not exert antimicrobial effect, a majority of silver compounds possess antimicrobial property. Empirically, the Romans in Europe and Indians in Asia have used this knowledge for centuries. In ancient Rome it was common practice to add silver coins to large cisterns of water to improve potability. And in India, the practices of storing clarified fats in silver vessels to prevent rancidity and of applying thin silver foil to sweets are still widespread. The thin foil silver surface protects the sweets from bacteria shed by house flies which are common in sweet shops in tropical India. The antimicrobial or bacteriostatic action in the use of silver coins or foil is due to minute quantity of ionic silver released from the oxidized layer on the silver surface, an effect known as oligo-dynamic action.

In modern medicine, towards the turn of $20^{th}$ century eye drops consisting of 1% silver nitrate solution were first employed to prevent blindness in newborns delivered by mothers suffering from sexually transmitted diseases. However, despite the tremendous potential of silver compounds as antimicrobials, commercial antimicrobial products that include silver have failed to materialize for several reasons. First, silver compounds containing products tend to degrade with time due to their photo-sensitive nature. This property of silver compounds also makes them thermally sensitive which in turn makes manufacturing products that include silver compounds very challenging. More often than not manufacturing processes involved are energetically very intensive. Second, more robust alternative to silver compounds in the form of antibiotics and other chemical based antimicrobials (xylenol derivatives and biguanides) were developed and have dominated the medical industry for over past fifty years or so. Nonetheless, despite the general limitations of silver compounds, several robust silver based technologies e.g. silver sulfadiazine, stabilized silver chloride, silver saccharinate, silver zeolites and silver zirconium phosphate have found applications in niche areas such as advanced wound care.

These silver technologies however, have their own limitations. For instance, silver sulfadiazine is practically insoluble in water. So, on w/w basis much higher content of the compound is required to exert therapeutically effective antimicrobial effect. And there have been reports of issues related to patient sensitivity to sulfonamides. Silver zeolites and silver zirconium phosphate due to their inorganic nature are unsuitable for inclusion in medical products that require implantation or contact with breached skin. Despite its promise, very few products based on silver saccharinate have been introduced in commerce.

Thus, there is a need for novel antimicrobial silver compounds or a group of silver compounds that form the basis of robust and effective antimicrobial silver technology that can overcome aforementioned limitations. More recently, a novel silver based technology including a group of silver cyanurate compounds was disclosed by the present inventor in the PCT/US2014/035945 application which is hereby incorporated in its entirety by reference for all purposes. The present invention expands upon that development and provides a new class of antimicrobial silver s-triazine compounds that may possess good light and heat resistance and may be readily incorporated in a variety of compositions and devices in both medical and non-medical settings. The said antimicrobial silver s-triazine compounds may possess broad spectrum antimicrobial activity against bacteria, yeast, fungi, viruses and other microorganisms.

SUMMARY OF THE INVENTION

The chemical structures of the antimicrobial silver compounds of the present invention are disclosed below.

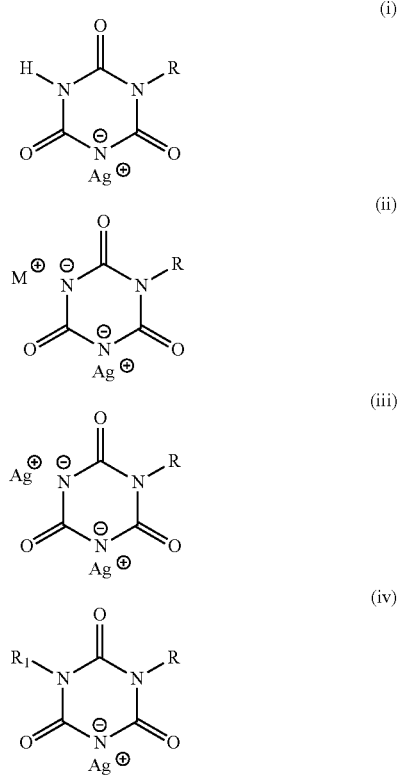

-continued

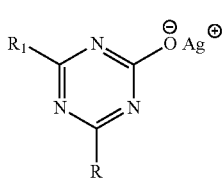
(v)

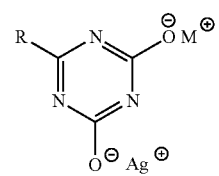
(vi)

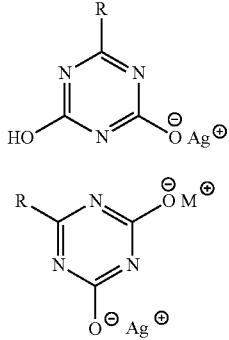
(vii)

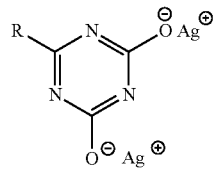
(viii)

Where R and R₁ can be any of the following groups:

Straight chain or branched alkyl with 1 to 20 carbon atoms, allyl, vinyl, phenyl, benzyl, napthyl, heteroaryl or substituted alkyl, phenyl, benzyl or heteroaryl and M is one of the following cations: sodium, potassium, lithium, quaternary ammonium, calcium, magnesium, copper, zinc and aluminum.

As a new class of antimicrobial s-triazine based compounds including silver, they resist discoloration induced by light and heat. The inventive compounds offer several advantages. The basic heterocyclic ring units (substituted s-triazines) may be relatively straightforward to synthesize given that starting materials such as biuret and primary amines are commodity chemicals and thus relatively inexpensive. The said antimicrobial s-triazine based compounds may be relatively non-toxic given the fact that metal salts (sodium) of heterocyclic base units in the past have been investigated extensively for medicinal applications as anticonvulsants. For instance, sodium salts of the lower di-alkyl substituted s-triazines reportedly have systemic $LD_{50}$ values for mice ranging between 500 and 3000 mg/kg body weight (U.S. Pat. No. 3,689,651). These metal salts may be easy to synthesize since the heterocyclic base units possess acidic protons that can be easily replaced. Another key feature of the said antimicrobial compounds may be the flexibility afforded to add different groups (R and R₁) that allow the modulation of properties of the compounds. Thus, one may dial in the duration desired for sustenance of antimicrobial activity by selecting specific R groups that may determine the compounds' solubility and hence the release characteristics. Notwithstanding the ability to change properties by changing R or R₁ substituents, certain compounds carry both cation M and Ag cation that may provide them with a wide range of aqueous solubility. Furthermore, those compounds with Cu and Zn cations complementing silver cation may induce galvanic action thereby enhancing the effectiveness of the antimicrobial character of the said compounds.

Another embodiment of the present invention are the metal salts of various s-triazine compounds with structures (ix) through (xiv) shown below possessing cation M from the following group: sodium, potassium, lithium, quaternary ammonium, calcium, magnesium, copper, zinc and aluminum. They undergo anion exchange reaction to yield antimicrobial silver s-triazine compounds with structures shown earlier.

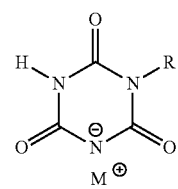
(ix)

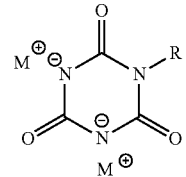
(x)

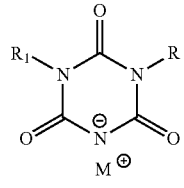
(xi)

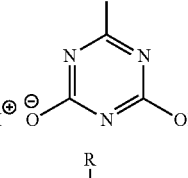
(xii)

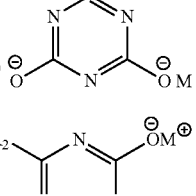
(xiii)

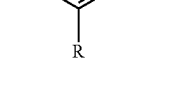
(xiv)

In general, the methods of preparing the antimicrobial compounds with structures (i) through (viii) are encompassed by the present invention. The methods include reacting the corresponding metal salts with structural formulas (ix) through (xiv) with a suitable soluble silver salt solution to affect anion exchange.

The antimicrobial compounds disclosed herein may be used to impart antimicrobial property to medical and non-medical devices and compositions. Examples of compositions include amorphous compositions such as lotions, creams, emulsions, hydrogels, aqueous and non-aqueous coatings, inks and paints. A non-limiting list of medical devices may include alginate non-woven sheets and ropes and similar water absorbent material (Aquacel®, Maxorb®), polyacrylamide based matrices such as Flexigel® sheet, thin film dressings to cover wounds, cellulose containing material such as cotton gauze, hydrocarbon based polymer (polyethylene, polypropylene), natural and synthetic polymers (with biodegradability and biosorbability) based compositions such as gels, emulsions, lotions or devices in the form of films, mesh and three dimensional objects. Additional medical and non-medical devices that may be imparted antimicrobial property with the inventive silver s-triazine compounds of the present invention are listed in paragraph 140 of US2007/0003603A1 which is included herein and is incorporated in its entirety by reference for all purposes or are disclosed in PCT/US2014/035945, also hereby incorporated by reference for all purposes. The inventive silver s-triazine compounds of the present invention may be used singly or in combination with other inventive silver s-triazine compounds of the present invention or with other known silver cyanurate compounds disclosed in PCT/US2014/035945 or other known silver compounds including silver nanoparticles and non-silver compounds to impart varying antimicrobial properties to the said inventive devices.

DETAILED DESCRIPTION OF THE INVENTION

Antimicrobial Silver s-Triazine Compounds

Figure 1:
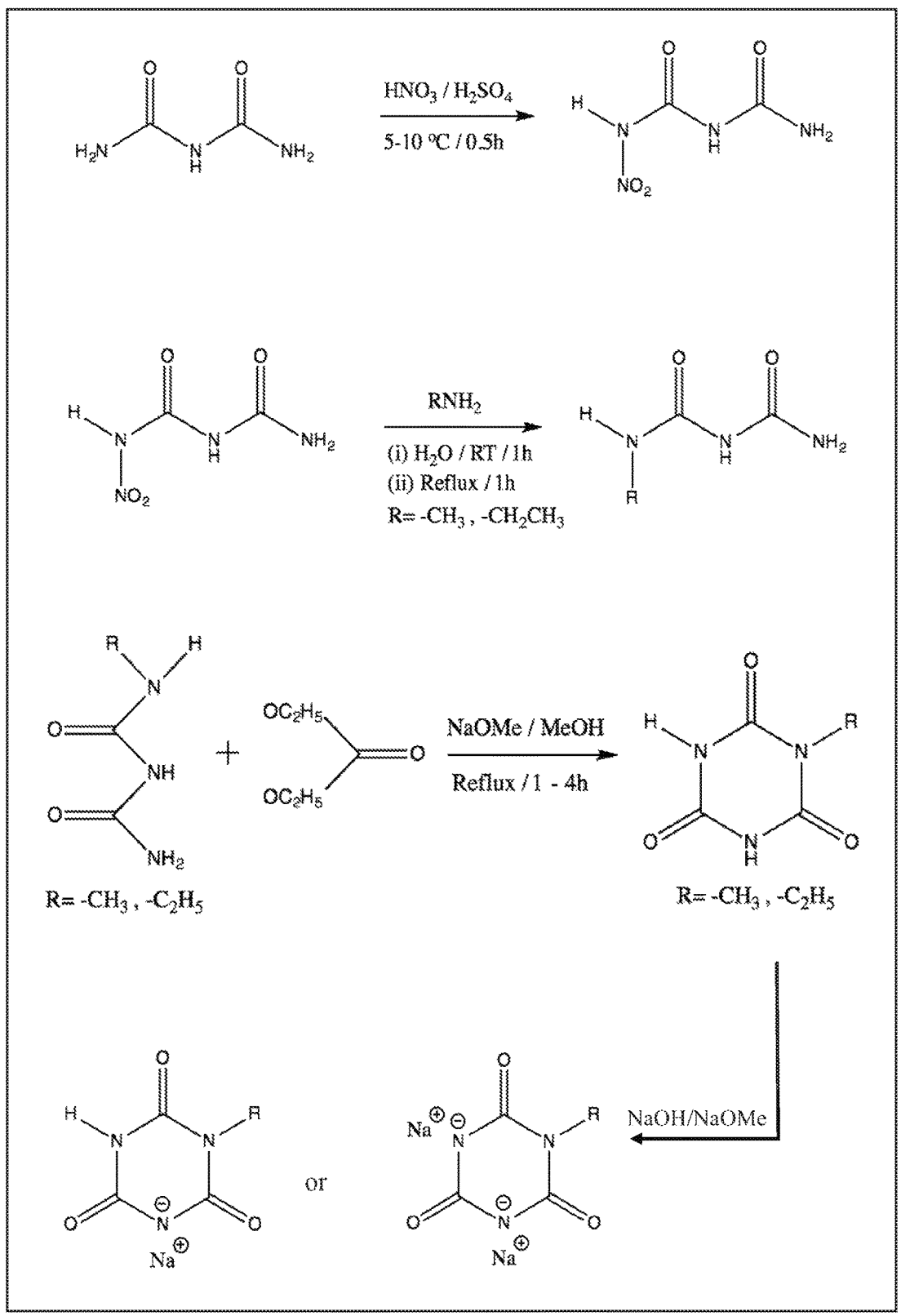
FIG. 1 illustrates methods of making sodium salts of mono-substituted isocyanuric acids (with different alkyl or aromatic substituents).

The present invention and its various embodiments will be discussed in detail below. The invention pertains to a new class of antimicrobial silver compounds comprising s-triazine ring that are distinct from the group of silver cyanurate compounds disclosed in the PCTUS2014/035945. The key distinction being the present inventive antimicrobial silver s-triazine compounds comprise s-triazine ring with at least one substituent that is other than hydrogen on N or C atom. More broadly, the present inventive silver compounds are derived from four types of s-triazine heterocyclic compounds; mono- and di-substituted isocyanuric acids where the substituents are on N atoms (s-triazine ring common to structures (ix), (x) and (xi) and mono-substituted di-hydroxy s-triazine (s-triazine ring common to structure (xii) and (xiii)) or di-substituted mono-hydroxy s-triazine (structure (xiv)) where the substituents are attached to C atoms. The chemical structures of the antimicrobial silver compounds of the present invention are represented in structures (i) to (viii) disclosed earlier.

Common to the structures shown is a symmetric triazine ring with key differences in positions on the triazine ring where the chemical substituents are present. Each of the heterocyclic moiety above is a modification of the cyanuric acid molecule shown below which is known as 1,3,5 triazine triol or as 1,3,5 triazinane 2,4,6 trione as per IUPAC nomenclature.

The cyanuric acid in solid form exists as Structure A and in solution as Structure B which is its tautomer.

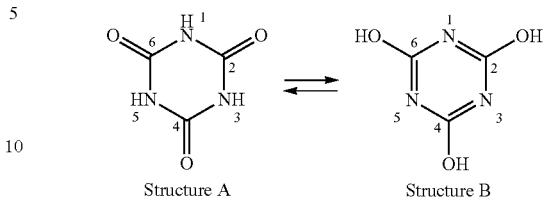

Structure A         Structure B

Substitution on N Atoms

The structure on the left above is also known as isocyanuric acid. Because of three sites available for chemical modification in isocyanuric acid, a large number of its derivatives can be synthesized. For example, each proton on N atom in Structure A may be replaced. Only single N atom of the triazine ring in Structures (i) to (iii) may carry an R substituent, thus basic triazine ring in those structures is mono-substituted isocyanuric acid. When 2 N atoms have substituents R or $R_1$, the result is di-substituted isocyanuric acid (Structure (iv)). The substituents R and $R_1$ in Structure (iv) may be identical or dissimilar.

Substitution on C Atoms

In the inventive silver s-triazine compounds, the C atoms in the s-triazine ring (Structure B) may carry any substituent that is not directly bonded to a heteroatom (O, N or S) in the substituent. When only one C atom is substituted the resulting triazine is a di-hydroxy s-triazine i.e. one hydroxyl group is replaced in Structure B above. With second C atom substituted, a mono-hydroxy s-triazine is obtained. The two substituents R and $R_1$ on C atoms may or may not be identical.

Properties of Antimicrobial Silver s-Triazine Compounds

Aside from their inherent antimicrobial properties due to the presence of silver, these compounds generally have good light and heat resistance. Without being bound by any theory, the inventor believes that the presence of tertiary nitrogen atoms of s-triazine rings may provide ligand type interactions with silver atoms thereby limiting pathways to photo-reduction of silver. These interactions between silver and N atoms may be intermolecular in nature which may lead to a large loosely bound molecular network. As a result, these compounds though presented as chemical structures (i) to (viii) may actually possess very complex structures. Regardless of this fact, the present inventive compounds are the products of anion exchange reactions between metal salts of s-triazine compounds with structures (ix) to (xiv) and soluble silver salt solution preferably in water or water rich solvent mixtures. The complexity of their actual structures makes these compounds relatively sparingly soluble in water or polar solvents, making their characterization by traditional means quite challenging.

Despite the complex intermolecular interactions, the substituents R or $R_1$ do permit the tailoring of a property, for instance, the solubility characteristics of the inventive antimicrobial compounds. For instance, a long chain alkyl or an aromatic ring substituent will lead to increased solubility in nonpolar solvents or will lead to improved compatibility with hydrocarbon rich polymers such as polyethylene (PE) and polypropylene (PP). Certain groups may help with improved emulsification behavior. However, the complex intermolecular interactions between silver and N atoms will still exert their effects generally maintaining low solubility in water of the antimicrobial silver compounds. On the other hand, the hydrophobic substituents and the intrinsic polar character of the s-triazine ring may provide contrasting properties and may lead to unusual properties of the solutions of its metal salts or suspensions of silver s-triazine compounds.

Under Scanning Electron Microscope (SEM), silver-DMCA (see Acronyms section for details) and silver-MIC compounds exhibited long fiber or rod like morphology with diameter ranging between 100 nm and lengths running into several microns. The silver-EIC compound exhibited a unique morphology of microcrystals with rose like structure with petal like layers of 100 nm thickness. The silver-PDT compound was crystalline as well exhibiting rod like appearance but these rods possessed micron size dimensions.

The solubility in water at 25° C. of antimicrobial silver compounds of DMCA, EIC, MIC and PDT respectively was determined by analyzing the corresponding saturated solutions for silver by Atomic Absorption Spectroscopy. The aqueous solubility values at 25° C. respectively were found to be 654, 16.5, 48 and 18 mg/liter.

Metal Salts of s-Triazine Derivatives

Another aspect of the present invention are the metal salts of substituted s-triazine compounds with structures (ix) to (xiv) where the metal cations may be any of the following cations: sodium, potassium, lithium, quaternary ammonium, calcium, magnesium, copper, zinc and aluminum. Metal salts are possible because the substitution at N atoms in mono- or di-substituted isocyanuric acids or at C atoms in mono- or di-hydroxy triazines renders the remaining proton or protons acidic. As a result, the substituted isocyanuric acids and hydroxyl s-triazines form salts especially with alkali metals. While with cyanuric acid (Structure B) one can obtain a cyanurate salt with maximum of 3 metal cations, with mono-substituted isocyanuric acid, metal salts may carry either one or two cations. Similarly, a di-substituted isocyanuric acid can form salt having only one cation. Similarly, mono- and di-hydroxy s-triazines form metal salts that carry two and one cations respectively.

Thus, the metal salts of mono- and di-substituted isocyanuric acids and hydroxy s-triazine derivatives having chemical structures (ix) through (xiv) may be encompassed by the present invention. Some of the alkali metal salts of these s-triazine salts have been reported to have medicinal uses. But hitherto they have not been disclosed as starting materials in the preparation of inventive antimicrobial silver compounds of the present invention. In one embodiment, preferred metal salts are those of alkali and alkaline earth metals. Depending on the nature of the metal cation, the aqueous solubility of the metal s-triazine compound may vary. The alkali metal containing compounds are water soluble though others may only be partially or sparingly soluble.

Methods of Making Inventive Silver s-Triazine Compounds

The methods of preparing the inventive antimicrobial silver s-triazine compounds involve simple anion exchange between silver cation made available from soluble silver salt solution with metal cations of the corresponding metal salts of s-triazine compounds disclosed (see structures (ix) to (xiv)). The source of silver cation may be any silver salt having a water solubility of at least 5 g/liter at 25° C. In one embodiment, preferred silver salt is silver nitrate though other salts with biocompatible anions such as lactate, gluconate and acetate may be used. In one embodiment, among metal cations sodium, potassium and lithium may be preferred. In the case of metal salts that carry only single metal cation and when silver to metal cation mole ratio is 1:1, complete substitution may result (see structures (i), (iv), (v) and (vi)). In the case of mono-substituted s-triazine and or dihydroxy s-triazine one may obtain silver s-triazine compounds bearing two silver atoms (see structures (iii) and (viii)). In addition, if the silver cation to metal cation is maintained 1:2 then a mixed salt i.e. a compound bearing silver cation and a metal cation may result (see structures (ii) and (vii)).

In one embodiment, equal aliquots of equimolar aqueous solutions of sodium salt of s-triazine compound and silver nitrate solution are mixed in no particular order to precipitate out the corresponding silver s-triazine compound. In one example, preferred molarity of reagent solutions is 0.1M though other molarities may range between $10^{-5}$M and 1.0M and are within the scope of the invention. In another example, preferred conditions are ~20-25° C. and low lighting conditions. Though reaction temperature higher than ambient (up to 100° C.) and below ambient (5° C.) are encompassed by the invention. As s-triazine compounds are weakly acidic, anion exchange between the metal cations of the salts of s-triazine compounds and silver may not be instantaneous. Therefore, the reaction duration of the anion exchange may be as little as 1 min to as high as 24 h and will depend strongly on the temperature employed.

The reagents may or may not be combined in the presence of other ingredients e.g. polymer or other antimicrobial compounds. Both aspects are covered by the invention. In one embodiment, preferred solvent is water though aqueous solutions of lower alcohols ($C_1$ to $C_5$) and other aprotic solvents may be employed where the water content is at least 50% v/v. The resulting silver s-triazine compound may be separated from residual ionic impurities by traditional methods known to those ordinarily skilled in the art. The purified compound may be maintained as suspension or recovered as dry powder (neat or dispersed on inert inorganic matrices).

Thus, reacting the metal salts of substituted isocyanuric acid and hydroxy s-triazines with suitable soluble silver salt solutions, the inventive antimicrobial compounds may be obtained.

Methods of Making Metal Salts of s-Triazine Compounds

Another embodiment of the present invention are the methods of making metal salts of s-triazine compounds as starting materials for inventive antimicrobial silver compounds. As a non-limiting example, the scheme of making sodium salts of mono-substituted isocyanuric acids (with different alkyl or aromatic substituents) is shown in FIG. 1.

Mono-Substituted s-Triazines

As first step, 1-nitrobiuret was prepared by nitration of biuret in relatively decent yield. Biuret is commercially available though it contains about 10% triuret. Despite the impurity in starting biuret, the nitrated product was recovered in relatively pure state and was used in the next step.

Next, 1-nitro biuret was condensed with corresponding primary amine (as aqueous solutions) with relative ease. The duration of reflux conditions was dependent on the nature of amine compound, though in the case methyl amine and ethyl amine, a couple of hours were sufficient. The alkyl substituted biuret as crystals was recovered by concentrating the reaction medium in moderate yields and used in a subsequent step.

The 1-alkyl substituted biuret was condensed with diethyl carbonate to form the sodium salt of mono alkyl substituted isocyanurate in the reaction medium. In the reaction scheme disclosed, we made some changes such as using commercially available sodium ethoxide instead of forming sodium ethoxide in situ from sodium and anhydrous ethanol. The reaction yield was low to moderate depending on the alkyl group. The crude sodium salt was recovered, acidified with concentrated hydrochloric acid to yield pure isocyanuric acid. As needed, the sodium salt of isocyanuric acid was prepared again by reacting the acid with sodium ethoxide in non-aqueous solvent medium. For disodium salt derivative, the mole ratio of sodium alkoxide or sodium hydroxide to s-triazine is maintained 2 to 1.

As specific illustrative non-limiting examples, we prepared the sodium salts of mono-substituted isocyanuric acid with methyl and ethyl groups. Those ordinarily skilled in the synthetic organic chemistry can readily prepare sodium salts of isocyanuric acid with other substituents following the reaction scheme described. Metal salts of substituted isocyanuric acids with cations other than sodium can be prepared starting with sodium salt solution by carrying out anion exchange reaction to replace sodium with the desired cation.

Di-Substituted s-Triazines

Figure 2:
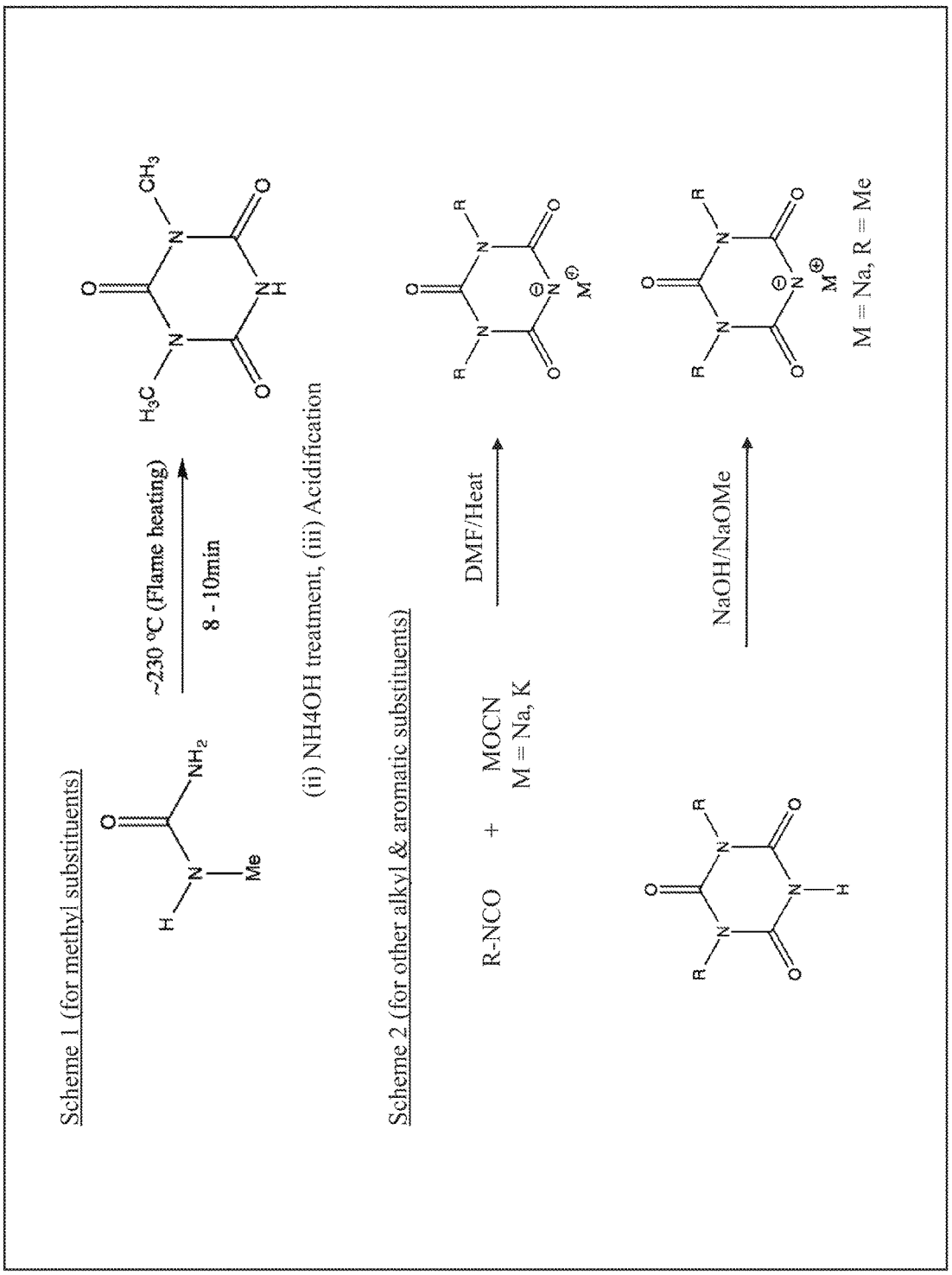
FIG. 2 illustrates two approaches for preparing di-substituted isocyanuric acid metal salts.

There are two approaches for preparing di-substituted isocyanuric acid metal salts as shown in FIG. 2. In scheme 1, 1-methyl urea is condensed to symmetric di-substituted isocyanuric acid in moderate yield. The reaction workup is relatively straightforward and yields pure compound. The scheme may be suitable for preparing dialkyl isocyanuric acid with ethyl or higher alkyl substituents though we did not attempt to prepare them. In scheme 2, which is more general in nature, di-substituted isocyanuric acid is obtained by reacting appropriate organic isocyanate with alkali metal cyanate in dipolar aprotic solvent at elevated temperatures. The preparative method is suitable for making di-substituted isocyanuric acid with aromatic and aliphatic groups. Metal salts can be made by treating the acid with corresponding alkali solutions or alkali metal alkoxides in appropriate mole ratio.

Hydroxy s-Triazine Derivatives

Figure 3:
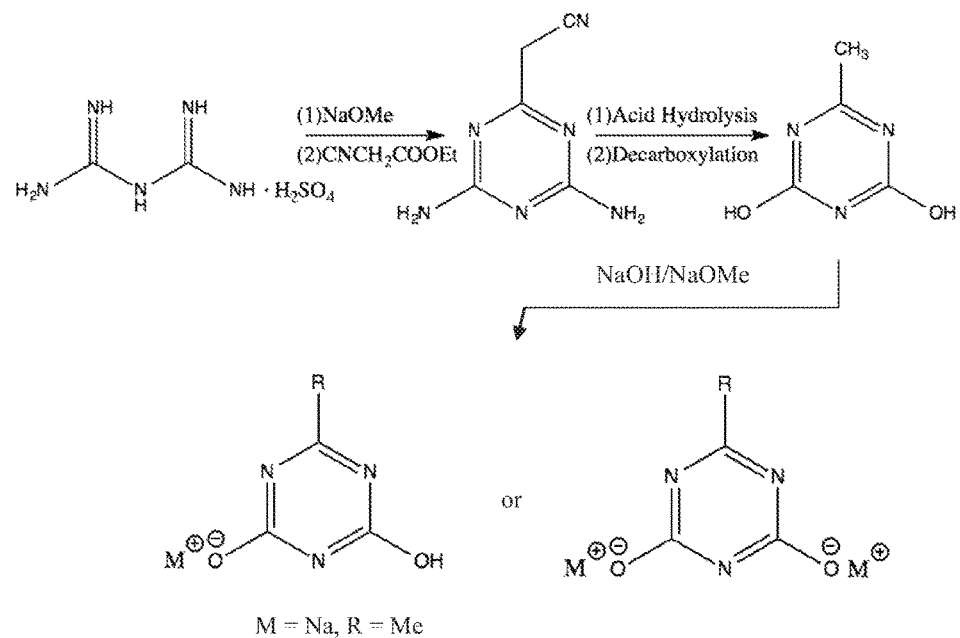
FIG. 3 illustrates methods for preparing two specific di-hydroxy s-triazines, one with aromatic group and other with aliphatic group and their metal salts.

The schemes for preparing two specific di-hydroxy s-triazines, one with aromatic group and other with aliphatic group and their metal salts is shown in FIG. 3. Acid hydrolysis in sulfuric acid at elevated temperatures (110° C. to 125° C.) of commercially available 6-phenyl 2,4 diamino s-triazine leads to 6-phenyl 2,4 dihydroxy s-triazine in decent yield. Treating the resulting 6-phenyl 2, 4 di-hydroxy s-triazine with alkaline compound (sodium hydroxide, sodium carbonate or sodium alkoxide) yields a corresponding mono- or di-substituted metal salt depending on the mole ratio of alkali to hydroxyl compound. In the second scheme, biguanide sulfate is treated with sodium methoxide in methanol and resulting biguanide free base is condensed with ethyl cyanoacetate under reflux conditions to yield 6-cyanomethyl 2,4 diamino s-triazine. The cyanomethyl group upon acid hydrolysis and decarboxylation converts to methyl group to yield 6-methyl 2,4 di-hydroxy s-triazine. Mono- or di-substituted metal salts of 6-methyl 2,4, dihydroxy s-triazine can be obtained by further treatment with alkali metal bases in proper mole ratio.

Several s-triazines compounds were synthesized in the reduction to practice of the invention but they only served as illustrative examples and should not be construed as limiting. As those skilled in the art will recognize, modifications to the s-triazines can be easily made without departing from the scope of the present invention.

Additional Antimicrobial Silver s-Triazine Compounds of the Present Invention

There are several other antimicrobial silver s-triazine compounds encompassed by the present invention. The chemical structures of these novel silver s-triazine compounds are shown below.

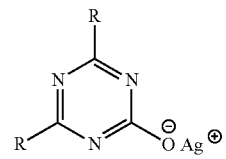

Structure C

Where R=L-R$_3$ where L independently may be one of the following:
L=—O— where O is oxygen,
=—S— where S is sulfur,
=—NH—,
=—(OCH$_2$CH(X))$_n$—O— where X=H or CH$_3$ and n=1-100,
and
R$_3$=H, linear or branched alkyl with 1 to 20 carbon atoms, phenyl, benzyl, heteroaryl or substituted phenyl or benzyl or heteroaryl.

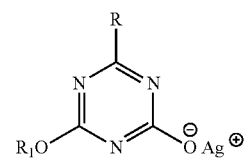

Structure D

Where R$_1$ independently is Ag or H, and
R=L-R$_3$ where L may be one of the following:
L=—O— where O is oxygen,
=—S— where S is sulfur,
=—NH—,
=—(OCH$_2$CH(X))$_n$—O— where X=H or CH$_3$ and n=1-100, and
R$_3$=H, linear or branched alkyl with 1 to 20 carbon atoms, phenyl, benzyl, heteroaryl or substituted phenyl or benzyl or heteroaryl, or
R is independently selected from the following group:
polyamides, polysiloxanes, polyurethanes, polyphosphazenes, polyesters, polyvinyl alcohol, polyallylamine, polallylalcohol, homopolymer of hydroxyethyl methacrylate (HEMA), homopolymer of hydroxyethyl acrylate (HEA), copolymer of HEMA with acrylamide, copolymer of HEMA with vinyl pyrrolidone, copolymer of HEMA with methacrylamide, copolymer of HEMA with substituted acrylamides, copolymer of HEMA with substituted methacrylamides, cellulose, cellulose ether polymers, alginate, hyaluronic acid, gums, gelatin, collagen, sugar alcohols, chitin, chitosan, cyclodextrin, dextrin, maltodextrin and biodegradable polymers derived from aminoacids.

Articles and Compositions Comprising Antimicrobial Silver s-Triazine Compounds

The utility of the inventive antimicrobial silver compounds lies in their broad spectrum antimicrobial activity against common pathogens including gram positive and gram negative bacteria, yeast, fungi, viruses and other lower forms of life. Another feature of these compounds is their relative non-toxicity towards humans and animals. They may also be effective against all antibiotic resistant strains. They may be included on surfaces or bodies of articles of manufacture including amorphous compositions and devices to impart antimicrobial property. The resulting antimicrobial articles comprising amorphous compositions and devices may be used directly in the treatment of humans and animals. Such devices specifically may include wound care products and a variety of implantable or non-implantable body contacting medical devices.

The inventive antimicrobial articles may also be employed in mitigating risk of transmission of bacteria among people in public settings and in maintaining organism free environments. Antimicrobial articles comprising said antimicrobial silver s-triazine compounds may also be employed in all non-medical settings and such use is within the scope of the present invention. The methods of incorporating said antimicrobial compounds in medical and non-medical devices are also encompassed by the present invention including compounding, formulating, dip-coating, spraying and vacuum deposition processes. The antimicrobial compounds may be used dry or wet or in dispersed form on inert inorganic matrices depending on the manufacturing convenience of the devices or compositions.

Illustrative non-limiting examples of preparing antimicrobial compositions or devices are listed in the following applications: PCT/US2014/035945 and PCT/US2005/27260, both incorporated by reference for all purposes. For example, in Example 17 of '260 application, aqueous suspension of silver s-triazine compound matching the silver content is added to the gel composition to prepare a gel with inventive silver s-triazine compound as the active. Similarly in other examples of '260 application, silver saccharinate may be replaced by the inventive silver s-triazine of the present invention.

An embodiment of amorphous composition comprising antimicrobial silver s-triazine compound may be an aqueous suspension or solution. Such suspension may be prepared by an anion exchange reaction between metal salt of s-triazine compound (in solution) with soluble silver salt in solution. The antimicrobial silver compound formed generally will precipitate given its low water solubility. In one embodiment, preferred method of making the suspensions is to conduct the anion exchange reaction with molarities of solution 0.05M or higher and then dilute the resulting concentrates of silver triazine compound to achieve lower content of silver though methods wherein the molarities lower than 0.05M are also within the scope of the invention. The amount of silver in such suspensions may vary from as low as 0.1 ppm to as high as 50,000 ppm. Even higher percentage of silver can be obtained by concentrating the dilute suspensions. Dilute suspensions may be used as disinfectant sprays and for sterilizing surgical tools where traditional methods of sterilization may not be readily available.

Antimicrobial Activity Testing

The antimicrobial activity of the antimicrobial silver s-triazine compounds was verified by standard zone of inhibition (ZOI) assay known to those skilled in the art. Briefly, in this assay, samples were placed on plates with proprietary agar formula (similar to Mueller Hinton Agar (MHA)) that were inoculated with bacteria and incubated at 37° C. overnight. If antimicrobial activity in the sample was present, it formed a clear zone around the edges. As negative control, the samples without the silver active compound were used. For primary screening of antimicrobial activity, the gram positive bacteria *Staphylococcus aureus* ATCC6538 was employed in the assay. To examine broad spectrum antimicrobial activity, various different types of organisms including gram negative *Pseudomonas aeruginosa* ATCC9027, Methicillin-Resistance *Staphylococcus aureus* (MRSA) and Vancomycin-Resistant Enterococci (VRE) could be employed. In investigating the broad spectrum activity, the ZOI assay is performed slightly differently. Instead of laying the samples on plates individually inoculated with different types of bacteria, the bacterial inoculums are streaked as parallel lines on one plate. After streaking the inoculum linearly, the samples are deposited as a continuous bead string in perpendicular direction to the streak lines. Evidence of antimicrobial activity in the sample is seen in the form of interruptions on both sides of the edges of the sample string.

Sterilization

The sterilization of any samples (devices or compositions) comprising antimicrobial silver s-triazine compounds was carried out by steam sterilization. By subjecting test samples to steam sterilization, one can ascertain the ability of the antimicrobial silver s-triazine compounds to withstand thermal stresses. The test samples experienced temperature rises from 20° C. to 122° C. over 15 min, followed by constant temperature of 122° C. for 15 min and finally a cool down from 122° C. to ~40° C. over 3 h. Thus, the test samples experienced nearly 3.5 h of hostile temperature condition.

Acronyms

DMCA Dimethyl cyanuric acid or Dimethyl isocyanuric acid
EIC Ethyl isocyanuric acid
MIC Methyl isocyanuric acid
PDT 6-Phenyl 2,4 di-hydroxy 1,3,5 triazine

ILLUSTRATIVE EXAMPLES

The present invention will be apparent to those ordinarily skilled in the art from the following non-limiting illustrative examples.

Syntheses of s-Triazine Compounds

Example 1: Preparation of 1-Nitro Biuret

To a 100 ml glass beaker with a magnetic stir bar, weighed quantities of concentrated sulfuric acid (20 g) and 70% nitric acid (5.0 g) were added in that order. The beaker was placed in glass trough filled with enough ice water mixture (5-10° C.) so that glass beaker would not float or tip. Biuret powder (4.12 g, FW103) was slowly added to the stirred acid mixture over several minutes. The powder went into solution to yield a clear solution that was stirred for 30 minutes. Using a plastic disposable pipet the acidic solution was dripped over crushed ice (~200 g) in another glass beaker. After all of the acidic mixture was added, the ice melted to yield a white suspension. After filtering the suspension, the resulting white solids collected were washed with ice water (~10° C., 200 ml). The filter paper with solids was dried in oven at 55° C. for ~2 h to recover cake of white solids (~3.75 g, Yield 64%). Recrystallization from 50/50 mixture of ethanol/water yielded pure crystals of 1-nitro biuret (~2.42 g). Elemental analysis confirmed the recovery of correct compound. Theoretical % C/H/N (16.22/2.70/37.84), Actual % C/H/N (16.54/2.65/37.76).

The above procedure was also employed for ~20-30 g scale preparation of 1-nitro biuret with appropriate prorating of reagents involved.

Example 2: Preparation of 1-Methyl Biuret

To a 100 ml flat bottom round flask with stir bar, 1-nitro biuret (8.74 g, 60 mmol) and deionized water (30 ml) were added. Under stirring, aqueous methyl amine solution (40% concentrate with ~12 mol/liter, 5.55 ml, 60 mmol) were added to the flask. Upon adding methyl amine solution, the suspension of 1-nitro biuret became more smooth thick paste like. The resulting solution was stirred at ambient for an hour followed by heating and reflux for an hour. About 15 minutes into reflux, the thick paste like suspension turned clear and remained that way during the rest of reflux. After reflux, the hot solution was quickly transferred to a crystallizing dish that was kept in oven at 45° C. to concentrate. After 1 to 1.5 h in the oven, crystals began to form in the crystallizing dish. At this point, the dish was moved to cool to room temperature. The dish was covered with plastic film and transferred to refrigerator to form more crystals overnight. With the help of a transfer pipet, remaining liquid in the dish was removed to another beaker and the crystals were dried in oven at 45° C. for 0.5 h. The amount of crystals (colorless to white) of 1-methyl biuret were ~4.86 g (Yield: 69%). Theoretical % C/H/N (30.77/5.98/35.90), Actual % C/H/N (30.75/5.95/35.80).

Example 3: Preparation of 1-Ethyl Biuret

To a 100 ml flat bottom round flask with stir bar, 1-nitro biuret (2.96 g, 20 mmol) and deionized water (30 ml) were added. Under stirring, aqueous ethyl amine solution (70% concentrate, 1.67 ml, 20 mmol) were added to the flask. Upon adding ethyl amine solution, the suspension of 1-nitro biuret in water immediately turned to pale yellow brown colored clear solution. The resulting solution was stirred at ambient for an hour followed by heating and reflux for a total of 40 minutes. The solution was cooled to room temperature and then transferred to a crystallizing dish. When the liquid in the dish concentrated to ~5 ml, crystals began to form. The dish was left in the hood overnight. The solids in the dish were wetted with ethyl acetate-methanol mixture (10 ml/1 ml); the resulting mixture was filtered to recover solids that were dried at 45° C. for 15 minutes. More solids were recovered from the filtrate as well. The total amount of solids crystals (cream colored) was ~1.12 g (Yield 43%). Theoretical % C/H/N (36.64/6.87/32.06), Actual % C/H/N (36.69/6.87/31.89).

Example 4: Preparation of Ethyl Isocyanurate

To a 100 ml flat bottom round flask with stir bar, sodium ethoxide (2.04 g) and anhydrous methanol (15 ml) were added followed by 1-ethyl biuret powder (1.97 g) and diethyl carbonate (3.54 g/3.62 ml). Another aliquot of anhydrous methanol (10 ml) was used to wash off solids off the stem of the flask into the solution. The contents were stirred to a clear pale orange solution that was heated to reflux. About 15 minutes of reflux caused the solution to become turbid and nearly 1.5 h of reflux turned the flask contents to nearly white viscous suspension. After 1.5 h reflux, the flask was cooled to room temperature. The flask contents were divided into 4 equal aliquots in 4 fifty ml polypropylene tubes. Ethyl acetate was added to each tube (25 ml) to precipitate out as much solids as possible. The tubes were centrifuged at 1200 rpm for 10 minutes and supernatant discarded. To wet solids at tube bottom, n-hexane (50 ml) was added to each tube and the resulting suspension was filtered and the solids dried in oven at 45° C. for several hours to yield off white to yellow of solids of sodium salt of ethyl isocyanurate (2.20 g, Yield 82%). The crude sodium salt was dissolved in deionized water (8 ml) and acidified to pH 3 to 4 with concentrated hydrochloric acid to precipitate out ethyl isocyanurate. The cream colored solids were filtered and dried in oven at 45° C. for 1 h (0.65 g, Yield 28%). Pure ethyl isocyanurate was recrystallized from methanol. Theoretical % C/H/N (38.22/4.46/26.75), Actual % C/H/N (38.36/4.59/26.42).

Example 5: Preparation of Methyl Isocyanurate

A procedure employed for ethyl isocyanurate was followed for preparing methyl isocyanurate on 20 mmol scale. The amount of methyl isocyanurate recovered was 1.83 g (Yield: 64%). Pure methyl isocyanurate was recrystallized from methanol. Theoretical % C/H/N (33.57/3.50/29.37), Actual % C/H/N (33.65/3.56/29.31).

Example 6: Preparation of Dimethyl Cyanuric Acid 1-methyl urea (2 g, 27 mmol) powder was transferred to a 100 ml round bottom glass flask and heated inside a hood on open flame of n-butane burner for 8 to 10 minutes. Heating caused the solids to melt and white fumes engulfed the flask during the heating phase. The heating was discontinued when we observed a trace of yellow to the melt in the flask. The contents were cooled to room temperature. To the fused mass in the flask, ammonium hydroxide (7.5 ml, 2M) were added. The contents were swirled to aid dissolution of solids to clear solution. The alkaline solution was acidified with concentrated sulfuric acid to obtain a white suspension. The suspension was filtered to recover fine white powder upon drying (0.6 g, 28%). Recrystallization from aqueous methanol (40% v/v) gave rod like crystals of dimethyl cyanuric acid. Theoretical % C/H/N (38.22/4.96/26.75), Actual % C/H/N (37.94/5.14/26.68).

Example 7: Preparation of Sodium Salt of Methyl Isocyanurate, Ethyl Isocyanurate & Dimethyl Cyanuric Acid Sodium Dimethyl Cyanurate Dimethyl cyanuric acid (0.51 g, 3.24 mmol) and sodium ethoxide (97%, 0.227 g, 3.24 mmol) were successively added to anhydrous methanol (20 ml) in a 100 ml flat bottom flask with a magnetic stir bar. Initially, cyanuric acid did not dissolve in methanol but after ethoxide addition, it briefly went into solution followed by the appearance of a fine white solid. The amount of white solid continued to increase turning the pale orange colored suspension to practically white. After 3 h stirring at room temperature, the suspension was filtered. The filtrate was transferred to a crystallizing dish to form very fine rod like crystals of sodium salt overnight. The crystal were washed with ethyl acetate/methanol (9:1) mixture (30 ml), filtered and recovered after drying at 45° C. for ~1 h. The yield was quantitative. Theoretical % C/H/N/Na (33.52/3.35/23.46/12.85), Actual % C/H/N/Na (31.37/3.90/21.34/13.10).

Sodium Salt of Ethyl Isocyanurate

The procedure was identical to that employed for making sodium salt of dimethyl cyanuric acid. On the basis of 4 mmol of starting material, ethyl isocyanurate, the yield of fine rod like crystals of sodium salt was ~70%. Theoretical % C/H/N/Na (33.52/3.35/23.46/12.85), Actual % C/H/N/Na (32.11/3.64/22.27/11.40).

Sodium Salt of Methyl Isocyanurate

The procedure was identical to that followed for synthesizing sodium salt of ethyl isocyanurate. The yield was ~90%. Theoretical % C/H/N/Na (29.09/2.42/25.45/13.94), Actual % C/H/N/Na (28.14/2.85/24.09/12.50).

Example 8: Preparation of 6-Phenyl 2,4 Dihydroxy 1,3,5 Triazine

The compound was synthesized with slight modification of the example in U.S. Pat. No. 3,340,261 which is incorporated herein its entirety by reference. The amount of compound recovered after drying as white caked solid was 11.80 g (Yield: 85%). The compound was crystallized as fine rod like crystals from 50/50 mixture of methanol-water with half molecule of water of crystallization. Theoretical % C/H/N (54.49/4.03/21.19), Actual % C/H/N (54.52/4.21/21.14).

Example 9: Preparation of Sodium Salt of 6-Phenyl 2,4 Dihydroxy 1,3,5 Triazine 6-Phenyl 2,4 dihydroxy 1,3,5 triazine crystals (1.0 g, 5.3 mmol) and sodium carbonate (0.28 g, 2.64 mmol) were transferred to a 200 ml glass beaker containing deionized water (50 ml). The contents were heated to dissolution on a hot plate for 0.5 h maintaining temperature 70-75° C., then cooled to room temperature to obtain fine rod like crystals. Additional cooling in refrigerator increased crystals yield. The crystals were recovered by filtration and drying at 55° C. for 1 h after washing with methanol. The amount of solids obtained was 0.71 g (Yield: 63%). Two molecules of water of crystallization were associated with the sodium salt. Theoretical % C/H/N/Na (43.69/4.05/16.99/9.30), Actual % C/H/N/Na (43.43/4.22/16.74/8.25).

Example 10: Preparation of Silver Compounds of Dimethyl Cyanuric Acid (DMCA), Ethyl Isocyanurate (EIC), Methyl Isocyanurate (MIC) and 6-Phenyl 2,4 Dihydroxy 1,3,5 Triazine (PDT)

Solutions of sodium salts of DMCA, EIC, MIC and PDT each with 0.1M concentration were prepared by dissolving appropriate amounts of corresponding salts in deionized water in PP tube with slight warming in microwave oven. Each solution exhibited pH~9 which indicated that the corresponding triazine compounds were weakly acidic. In preparing corresponding silver compounds, equal volume aliquots (1 ml each) of 0.1M sodium salt solutions of corresponding triazine compounds and 0.1M silver nitrate were mixed in dark conditions in PP tubes. To prepare silver DMCA compound, the tube contents were held at 55° C. for 10 min while to obtain silver compounds of EIC and MIC required heating for 2 h at 55° C. In each case, white silver compounds obtained were washed with deionized water to remove other ionic impurities and dried at 45° C. Antimicrobial Articles & Compositions

Example 11: Gel Made Comprising Silver-PDT Compound @ 550 ppm Silver

Powdered active silver compound was first prepared. An aliquot of 0.1M silver nitrate was added to equal aliquot of 0.1M mono-sodium PDT solution to precipitate out the silver compound. The reaction mixture was left overnight and recovered by washing with deionized water three times and filtering the solution and drying the resulting white solids.

To a 100 ml PP cup, sodium carboxymethyl cellulose (9H4F grade from Ashland Chemical Co.) (0.4 g), glycerol (2 g) were added followed by hot water (17.5 ml) and the contents hand-mixed to a smooth viscous mass. Silver-PDT powder (~0.027 g) was transferred to the gel and hand-mixed to uniformity with a spatula to obtain clear to hazy gel. Small quantity of the gel in PP tubes was exposed to direct sunlight, no discoloration of gel was seen for up to an hour. Short term exposure to 55° C. did not show any gel discoloration.

Example 12: Aqueous Suspensions of Ag-PDT, Ag-DMCA, Ag-EIC and Ag-MIC Compounds A white suspension of silver-PDT was obtained by mixing equal volumes of 0.1M silver nitrate solution into 0.1M monosodium PDT solution in the dark. Similarly, undiluted suspensions (white in color) were prepared in 15 ml PP tubes from 0.1M silver nitrate solution and sodium salt solution of DMCA, monosodium salt solutions of EIC and MIC respectively. The tubes were maintained at 55° C. for 2 h to complete anion exchange in the case of EIC and MIC. For DMCA, the tube was kept at ~25° C. overnight for reaction completion. Undiluted suspensions of silver-DMCA, silver-EIC and silver-MIC exposed to direct sunlight withstood 3 h, 1.5 and 1.5 h of exposure respectively, before any sign of discoloration was noticed. Considering that the amount of silver in the undiluted suspensions was ~5500 ppm, the discoloration resistance can be considered extraordinary. In contrast, the undiluted suspension of Ag-PDT withstood 0.5 h of sunlight exposure before discoloration was visible. But when the suspension was diluted with deionized water to give theoretical silver content of ~1350 ppm, over 4 h of direct sunlight exposure was required before the suspension in PP tube showed signs of discoloration. During photo-exposure, the diluted suspension temperature increased to ~50° C. yet no discoloration was seen.

Example 13: Solutions of Ag-DMCA, Ag-EIC and Ag-MIC in the Presence of Ammonia Stock solutions (0.1M) of monosodium salts of DMCA, EIC and MIC were prepared. In 15 ml PP tubes, suspensions of Ag-DMCA, Ag-EIC and Ag-MIC were prepared separately. To accelerate anion exchange between sodium and silver cations, heating of liquids was carried out in microwave between ~50° to 55° C. The tube contents were cooled and then to each tube neat ammonium hydroxide (0.1 ml) was added which caused the suspensions to clear for all three compounds. The resulting compounds when exposed to table lamp light (at a distance of 12"), no discoloration of the clear solutions was observed for 96 h for Ag-DMCA and Ag-EIC and for 72 h for Ag-MIC. The theoretical content of silver in the clear solutions was ~5000 ppm.

Example 14: Preparation of Woven Cotton Gauze & Paper Impregnated with Ag-MIC A suspension of Ag-MIC was prepared according to Example 13. A small quantity of the suspension (0.4 ml) was diluted with deionized water (2 ml) and neat ammonium hydroxide (~0.1 ml) was added to obtain a clear solution. A 2"×2" piece of cotton gauze was soaked in the clear solution, blotted with paper towel to remove excess and dried at 55° C. for 0.25 to 0.5 h. In the same clear solution prepared separately, a filter paper strip was immersed, shaken and then dried at 55° C. for 0.25 h-0.5 h. Both substrates with silver-MIC were exposed to direct sunlight. The gauze showed no discoloration even after 3 h whereas the paper strip registered a faint cream color after 1.5 h. Thus, in both instances following substrate impregnation, Ag-MIC still maintained robust light discoloration resistance.

Example 15: Amorphous Gel Composition with Ag-MIC @ 550 ppm Silver

To a 100 ml PP cup with stir bar, deionized water was added (13.2 ml). Under stirring Laponite XLG powder (0.8 g) was added and stirring continued for 10 to 15 minutes to form a thixotropic gel. Next, glycerol (2.0 g) was added and hand-mixed in with a spatula, followed by MIC solution (0.1M, 2 ml) that was hand-mixed and finally Ag-MIC suspension (2 ml) made according to the Example 010-32. The viscous slightly hazy gel did not discolor following overnight table lamp light exposure. When exposed to 55° C. for 4 weeks, it was practically unchanged.

Example 16: Sodium Silicate Coating Composition with Ag-DMCA

A suspension of Ag-DMCA was prepared according to a method of Example 13. A small quantity of Ag-DMCA suspension (0.4 ml) was transferred to a 15 ml PP tube. To the tube, neat ammonium hydroxide (0.1 ml) was added that caused the suspension to turn clear. In a second 15 ml PP tube, sodium silicate (40% w/w, 2 g) was weighed in and to the silicate solution, clear Ag-DMCA solution was added and vortexed to uniformity. On a clean glass slide, a small volume (~0.25 ml) was spread with a transfer pipet and left in an oven at 55° C. to dry for 0.5 h. The theoretical amount of silver in the dried coating was estimated at ~2700 ppm. The hard slightly opaque coating was exposed to direct sunlight and did not show any discoloration after 1 h when the test was stopped. Such coating composition could be useful in providing antimicrobial surfaces.

Example 17: Alginate Sheet Dressing with Silver

An aliquot (0.4 ml) of the undiluted suspension of Example 12 was added to a 15 ml PP tube containing 95% ethanol (5.6 ml). The tube contents were vortexed to uniformity. With the help of a pipet, ethanol solution containing silver-PDT was dripped over a 2"×2" piece of alginate non-woven sheet dressing. The wet sheet was transferred to a nylon mesh that was place in an oven at 55° C. for drying for 0.5 to 1 h. Similarly, alginate sheet dressings (2"×2") impregnated with Ag-DMCA, Ag-EIC and Ag-MIC were prepared. The only difference was with Ag-EIC and Ag-MIC, small amount of ammonium hydroxide was added to solubilize the silver compounds. Otherwise, the dressings were made same as with Ag-PDT impregnated dressing. In all dressing samples made, the theoretical amount of silver was ~4500 ppm.

A smaller sample piece (1"×1") of each dressing was exposed to direct sunlight. After 1 h, when examined, the samples showed a hint of greying which demonstrated remarkable resistance to light induced discoloration. Similar sized piece of each dressing was pouched in foil and steam sterilized. After cooling to room temperature the samples were examined for discoloration. None was observed.

Example 18: Fibrous Substrate Impregnated with Ag-PDT Compound

A thin paper strip (4"×0.25") was soaked in the aqueous suspension of Ag-PDT prepared according to Example 12, excess shaken off and placed on a nylon mesh and dried at 55° C. for 0.5 h. Even after 4 h of direct sunlight exposure, no discoloration of the Ag-PDT impregnated paper was observed. The approximate theoretical amount of silver in the impregnated paper strip was ~8700 ppm.

Example 19: Antimicrobial Activity Testing of Prototypes

The antimicrobial activity of Ag-DMCA, Ag-EIC, Ag-MIC and Ag-PDT was verified qualitatively by ZOI assay. Each active silver compounds exerted strong activity against *Staphylococcus aureus* ATCC6538. The ZOI assay results are summarized below.

| Example | Test sample | Active silver compound | Zone width (mm) |
| --- | --- | --- | --- |
| 17 | Alginate sheet | Ag-DMCA | 7.0 |
| 17 | Alginate sheet | Ag-EIC | 8.5 |
| 17 | Alginate sheet | Ag-MIC | 9.5 |
| 17 | Alginate sheet | Ag-PDT | 5.5 |
| 14 | Cotton gauze | Ag-MIC | 5.5 |
| 14 | Filter paper | Ag-MIC | 8.0 |
| 19 | Cotton gauze | No silver | 0.0 |
| 19 | Filter paper | No silver | 0.0 |
| 15 | Gel | Ag-MIC | 2.5 |

Example 20: Broad Spectrum Antimicrobial Activity of Antimicrobial Silver s-Triazine Compounds (Prophetic)

In the example above, the activity was tested against a gram positive bacteria. However, given the inclusion of silver in the chemical structures of antimicrobial compounds of the present invention, each of them is expected to exert broad spectrum antimicrobial activity against a variety of gram positive and gram negative bacteria including Vancomycin-Resistant Enterococci (VRE), Methicillin-Resistant *Staphylococcus aureus* (MRSA), yeast, fungi or other lower forms of life. The broad spectrum activity is tested efficiently by modification of the ZOI assay as described in the antimicrobial testing section.

The invention claimed is:

1. An antimicrobial silver s-triazine compound consisting of:

silver with an s-triazine ring carrying at least one substituent R and/or R1 on a nitrogen atom;

wherein R and/or R1 is not hydrogen;

wherein the antimicrobial silver s-triazine compound has one of the following chemical structures:

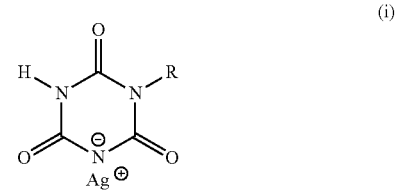

(i)

-continued

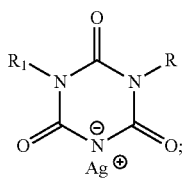
(iv)

wherein, for structure (iv), R and R1 include one of the group consisting of a straight chain alkyl group of 1 to 20 carbon atoms, a branched alkyl group of 0.1 to 20 carbon atoms, an allyl group, a vinyl group, a napthyl group, and a heteroaryl group when R and R1 are different;

wherein, for structure (iv), R and R1 include one of the group consisting of the straight chain alkyl group of 1 to 20 carbon atoms, the branched alkyl group of 1 to 20 carbon atoms, and the napthyl group when R and R1 are identical; and wherein, for structure (i), R includes one of the group consisting of the straight chain alkyl group of 1 to 20 carbon atoms, the branched alkyl group of 1 to 20 carbon atoms, the allyl group, the vinyl group, a phenyl group, a benzyl group, the napthyl group, and the heteroaryl group.

2. A method of making an antimicrobial silver s-triazine active agent, the method comprising steps of:
(i) preparing a solution of a metal salt of an s-triazine;
(ii) preparing a silver salt solution, where the silver salt solution comprises one of a silver nitrate solution, a silver lactate solution, a silver gluconate solution, and/or a silver acetate solution; and
(iii) reacting the solution of the metal salt of the s-triazine with the silver salt solution to obtain the antimicrobial silver s-triazine active agent
wherein the antimicrobial silver s-triazine active agent has one of the following chemical structures:

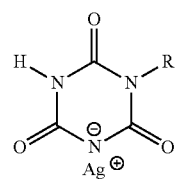
(i)

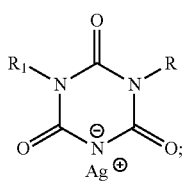
(iv)

wherein, for structure (iv), R and R1 include one of the group consisting of a straight chain alkyl group of 1 to 20 carbon atoms, a branched alkyl group of 1 to 20 carbon atoms, an allyl group, a vinyl group, a napthyl group, and a heteroaryl group when R and R1 are different;

wherein, for structure (iv), R and R1 include one of the group consisting of the straight chain alkyl group of 1 to 20 carbon atoms, the branched alkyl group of 1 to 20 carbon atoms, and the napthyl group when R and R1 are identical; and wherein, for structure (i), R includes one of the group consisting of the straight chain alkyl group of 1 to 20 carbon atoms, the branched alkyl group of 1 to 20 carbon atoms, the allyl group, the vinyl group, a phenyl group, a benzyl group, the napthyl group, and the heteroaryl group.

3. The method of claim 2, wherein the metal salt of the s-triazine comprises one of the following chemical structures:

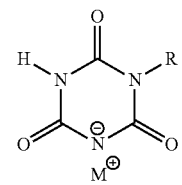
(ix)

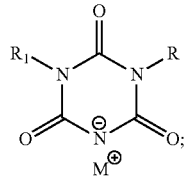
(xi)

wherein, for structure (xi), R and R1 include one of the group consisting of the straight chain alkyl group of 1 to 20 carbon atoms, the branched alkyl group of 1 to 20 carbon atoms, the allyl group, the vinyl group, the napthyl group, and the heteroaryl group when R and R1 are different;

wherein, for structure (xi), R and R1 include one of the group consisting of the straight chain alkyl group of 1 to 20 carbon atoms, the branched alkyl group of 1 to 20 carbon atoms, and the napthyl group when R and R1 are identical;

wherein, for structure (ix), R includes one of the group consisting of the straight chain alkyl group of 1 to 20 carbon atoms, the branched alkyl group of 1 to 20 carbon atoms, the allyl group, the vinyl group, the phenyl group, the benzyl group, the napthyl group, and the heteroaryl group; and wherein M is selected from the group consisting of sodium, potassium, lithium, quaternary ammonium, calcium, magnesium, copper, zinc, and aluminum.

4. The method of claim 2, wherein the metal salt of the s-triazine comprises a metal salt of mono-alkyl substituted s-triazine obtained by nitrating biuret to obtain 1-nitrobiuret;
chemically substituting the 1-nitrobiuret to obtain an alkyl substituted biuret; and
chemically reacting a 1-alkyl substituted biuret to form the metal salt of mono-alkyl substituted s-triazine.

5. The method of claim 2, wherein the metal salt of the s-triazine comprises a metal salt of di-substituted s-triazine obtained by heating 1-methyl urea to an elevated temperature to yield a di-substituted s-triazine, and treating the di-substituted s-triazine with an alkali solution to obtain the metal salt of di-substituted s-triazine.

6. The antimicrobial silver s-triazine compound of claim 1, wherein the at least one substituent R and/or R1 are selected as a function of a desired duration of sustenance of antimicrobial activity.

7. The antimicrobial silver s-triazine compound of claim 1, wherein the antimicrobial silver s-triazine compound is resistant to heat and light.

8. The antimicrobial silver s-triazine compound of claim 1, wherein the at least one substituent R and/or R1 are selected to tailor the antimicrobial silver s-triazine compound's solubility in nonpolar solvents and/or to improve the antimicrobial silver s-triazine compound's compatibility with hydrocarbon rich polymers.

9. The antimicrobial silver s-triazine compound of claim 1, wherein the at least one substituent R and/or R1 are selected to improve emulsification behavior of the antimicrobial silver s-triazine compound.

10. The antimicrobial silver s-triazine compound of claim 1, wherein the compound includes one of dimethyl cyanuric acid (DMCA), ethyl isocyanuric acid (EIC), methyl isocyanuric acid (MIC), and 6-phenyl 2,4 di-hydroxy 1,3,5 triazine (PDT); and wherein an aqueous solubility at 25° C. for each of DMCA, EIC, MIC, and PDT comprises 654 mg/L, 16.5 mg/L, 48 mg/L, and 18 mg/L, respectively.

11. The method of claim 2, wherein a silver to metal cation mole ratio is 1:1 for reacting the solution of the metal salt of the s-triazine with the silver salt solution to obtain the antimicrobial silver s-triazine active agent.

12. The method of claim 2, further comprising reacting the solution of the metal salt of the s-triazine with the silver salt solution at temperatures comprising 20° C.-25° C.

* * * * *